United States Patent [19]

Hopkins

[11] 4,168,882
[45] Sep. 25, 1979

[54] OPTICAL SYSTEMS

[75] Inventor: Harold H. Hopkins, Reading, England

[73] Assignee: The Secretary of State for Social Services in Her Britannic Majesty's Government of the United Kingdom of Great Britain and Northern Ireland, London, England

[21] Appl. No.: 866,912

[22] Filed: Jan. 4, 1978

Related U.S. Application Data

[63] Continuation of Ser. No. 681,599, Apr. 29, 1976, abandoned.

[30] Foreign Application Priority Data

Apr. 30, 1975 [GB] United Kingdom ............... 18074/75

[51] Int. Cl.$^2$ .......................................... G02B 23/00
[52] U.S. Cl. ...................................... 350/54; 350/179; 350/221; 350/222
[58] Field of Search .................... 350/45, 54, 179, 221, 350/222

[56] References Cited

U.S. PATENT DOCUMENTS

| | | | |
|---|---|---|---|
| 2,171,640 | 9/1939 | Berek | 350/222 |
| 3,257,902 | 6/1966 | Hopkins | 350/54 UX |
| 3,364,816 | 1/1968 | Jeffree | 350/179 X |
| 3,799,656 | 3/1974 | Fleischman | 350/222 |

Primary Examiner—John K. Corbin
Assistant Examiner—Matthew W. Koren
Attorney, Agent, or Firm—Cameron, Kerkam, Sutton, Stowell & Stowell

[57] ABSTRACT

An optical system for conveying an optical image having two first biconvex rod lenses arranged end to end on a common optical axis in spaced relationship, and between said first rod lenses but not in contact with them a pair of second rod lenses also arranged end to end on the same axis, the adjacent ends of the second rod lenses being concave and defining a biconvex cavity which can contain a fluid whereby a fluid lens is formed, the system being substantially symmetrical about a median plane through the biconvex cavity and the modulus of the reciprocal of the radius of curvature of the fluid lens being less than or equal to the modulus of the difference between the reciprocal of the radius of curvature of the convex surfaces of the first rod lenses adjacent to the second rod lenses and the reciprocal of the radius of curvature of the convex surfaces of the second rod lenses adjacent to the first rod lenses.

10 Claims, 3 Drawing Figures

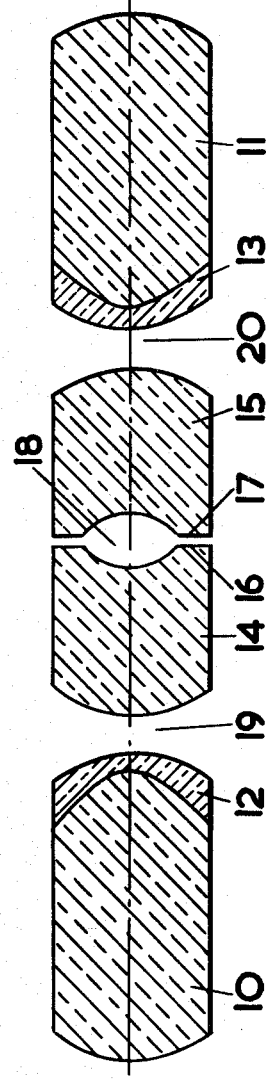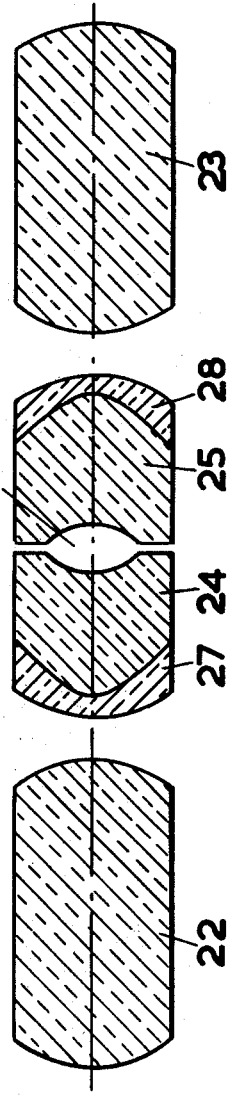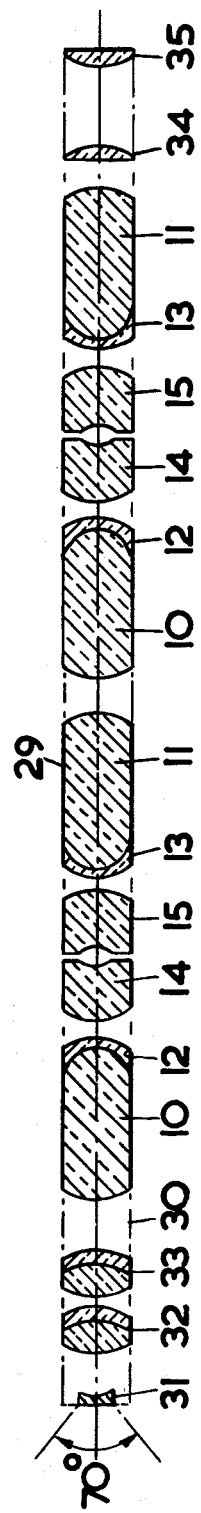

OPTICAL SYSTEMS

This is a continuation of application Ser. No. 681,599, filed Apr. 29, 1976, now abandoned.

This invention relates to optical systems and relates particularly to optical systems for relaying an optical image along a long, relatively narrow tube-like optical instrument, such as an endoscope.

When an optical image is relayed by a series of positive lenses, errors of field curvature and astigmatism may occur. One method of relaying an optical image along a tube is disclosed in U.S. Pat. No. 3,257,902 in which at least two rod lenses are used to convey an image. Such a method can be used in an instrument to view a useful field with acceptably small astigmatism and image curvature, and is particularly described in the specification with reference to a cystoscope. If this system is used for a laparoscope, in which wider angles of view and higher apertures are employed, the aberrations may not be corrected adequately, especially if a photographic record is required.

According to the invention, an optical system for conveying an optical image comprises two first biconvex rod lenses arranged end to end on a common optical axis in spaced relationship and between said first rod lenses but not in contact with them a pair of second rod lenses also arranged end to end on the same axis, the adjacent ends of the second rod lenses being concave and defining a biconvex cavity which can contain a fluid whereby a fluid lens is formed, the system being substantially symmetrical about a median plane through the biconvex cavity and the modulus of the reciprocal of the radius of curvature of each surface of the fluid lens being less than or equal to the modulus of the difference between the reciprocal of the radius of curvature of each of the convex surfaces of the first rod lenses adjacent to the second rod lenses and the reciprocal of the radius of curvature of each of the convex surfaces of the second rod lenses adjacent to the first rod lenses.

Preferably the axial length of each of the second pair of rod lenses is greater than 0.8 times the numerical value of the radius of curvature of each surface of the fluid lens.

To provide further correction of any optical errors, and more particularly the chromatic aberration, meniscus lens elements may be arranged one in each space between the first and second rod lenses and each meniscus lens element may be attached either to an end of a first rod lens or to an end of a second lens, the meniscus lens elements having a higher refractive index than the lenses to which they are attached. The refractive index of the second rod lenses should be not greater than 1.55.

The fluid comprising the fluid lens may, for example, be air or water and the fluid may also fill any spaces axially between the first and second rod lenses.

The curvature of the fluid lens in relation to the curvature of the adjacent convex surfaces of the first and second rod lenses can be expressed in mathematical terms as follows:

$$|C5| \leq |C3 - C4|$$

C3 being the curvature (=1/radius) of the convex surface of the first rod lens adjacent to the second rod lens, C4 being curvature of the convex surface of the second rod lens adjacent the first rod lens and C5 being the curvature of each surface of the fluid lens.

The customary cartesian convention for the sign of curvature of a surface is that the sign is positive if the centre of curvature is to the right of the surface and negative if the centre of curvature is to the left of the surface.

One or more systems according to the invention may be used to relay an image along a tube-like optical instrument such as an endoscope.

The invention will now be described by way of example with reference to the drawings filed herewith in which:

FIG. 1 illustrates in section one form of optical system according to the invention.

FIG. 2 illustrates in section an alternative form of optical system; and FIG. 3 illustrates diagrammatically use of the system shown in FIG. 1 in an endoscope.

In FIG. 1, two first biconvex rod lenses 10, 11 each have attached at one end a negative meniscus element 12, 13 respectively. Between lenses 10,11 are two second rod lenses 14, 15 the adjacent faces of which 16, 17 are partially concave and which define a biconvex air lens 18. The meniscus elements 12, 13 are separate axially from the second rod lenses, 14,15 by air gaps 19, 20.

The full specification of the optical system shown in FIG. 1 is given in Table I below:

Table I

|  | Radius mm | Axial thickness mm | Refractive index | Dispersion |
|---|---|---|---|---|
| Rod lens 10 | 12.752 |  |  |  |
| and meniscus | −5.36 | 28.179 | 1.5168 | 64.17 |
| element 12 | −9.528 | .248 | 1.68893 | 31.18 |
| Air gap 19 |  | 0.312 | 1 | 0 |
|  | 5.870 |  |  |  |
| Rod lens 14 |  | 4.327 | 1.5168 | 64.17 |
|  | 4.075 |  |  |  |
| Air lens 18 |  | 0.512 | 1 | 0 |
|  | −4.075 |  |  |  |
| Rod lens 15 |  | 4.327 | 1.5168 | 64.17 |
|  | −5.870 |  |  |  |
| Air Gap 20 |  | 0.312 | 1 | 0 |
| Maniscus | 9.528 |  |  |  |
| element 13 | 5.369 | 1.248 | 1.68893 | 31.18 |
| and rod lens 11 | −12.752 | 28.179 | 1.5168 | 64.17 |

In FIG. 2, two first rod lenses 22, 23 are arranged with two second rod lenses 24, 25 between them, the lenses 24, 25 each having a concave surface, which surfaces define a biconvex air lens 26. To the lenses 24, 25 are attached meniscus elements 27, 28 respectively.

In FIG. 3 an endoscope 29 comprises a tube containing at one end a negative lens 31 and biconvex lenses 32, 33 forming an objective lens system. The endoscope contains typically five of the optical systems shown in FIG. 1 or FIG. 2 although only two are shown in detail, as references 10 to 15, and also contains eyepiece lenses 34, 35. The lenses are spaced in the tube by annular spacers (not shown). Such an endoscope may have an angle of field equal to 70°.

In general an optical system according to the invention is suitable for use when an image is to be relayed along a tube of diameter much less than its length. In a typical case the diameter would be less than 10 mm, and the length would be substantially greater than the diameter, for example by a factor of ten or more. The system is applicable to any endoscopes, such as, for example, cystoscopes and bronchoscopes.

I claim:

1. An optical system of unit magnification for relaying an optical image having two first biconvex rod lenses arranged end to end on a common optical axis in spaced relationship, and between said first rod lenses but not in contact with them a pair of second rod lenses also arranged end to end on the same axis, the adjacent ends of the second rod lenses being concave and defining a biconvex cavity adapted to contain a fluid, whereby a fluid lens is formed, and the other ends of said second rod lenses being convex, the system being substantially symmetrical about a median plane through the biconvex cavity and the modulus of the reciprocal of the radius of curvature of each surface of the fluid lens being less than or equal to the modulus of the difference between the reciprocal of the radius of curvature of each of the convex surfaces of the first rod lenses adjacent to the second rod lenses and the reciprocal of the radius of curvature of each of the convex surfaces of the second rod lenses adjacent to the first rod lenses.

2. An optical system according to claim 1 in which the axial length of each of the pair of second rod lenses is greater than 0.8 times the numerical value of the radius of curvature of each surface of the fluid lens.

3. An optical system according to claim 1 in which meniscus lens elements are arranged one in each space between first and second rod lenses.

4. An optical system according to claim 3 in which at least one of said meniscus lens elements is attached to an end of one of said rod lenses, the refractive index of the meniscus lens element being higher than that of the rod lens to which it is attached.

5. An optical system according to claim 1 in which the refractive index of the second rod lenses is not greater than 1.55.

6. An optical system according to claim 1 in which the fluid of any fluid lens is air.

7. An optical system according to claim 1 in which the fluid of any fluid lens is water.

8. An optical system according to claim 7 in which any spaces axially between the first and second rod lenses are filled with water.

9. An optical system according to claim 1 in which any spaces axially between the first and second rod lens are filled with air.

10. An endoscope having an objective lens, an eyepiece, and an optical system according to claim 1 interposed between said objective lens and said eyepiece.

* * * * *

UNITED STATES PATENT AND TRADEMARK OFFICE
CERTIFICATE OF CORRECTION

PATENT NO. : 4,168,882
DATED : Sept. 25, 1979
INVENTOR(S) : Harold H. HOPKINS

It is certified that error appears in the above-identified patent and that said Letters Patent are hereby corrected as shown below:

Column 2, (Table I), line 32, ".248" should read -- 1.248 --.

Signed and Sealed this

Eighteenth Day of March 1980

[SEAL]

Attest:

SIDNEY A. DIAMOND

Attesting Officer     Commissioner of Patents and Trademarks